US006623433B2

(12) United States Patent
Webler et al.

(10) Patent No.: US 6,623,433 B2
(45) Date of Patent: *Sep. 23, 2003

(54) AUTOMATED LONGITUDINAL POSITION TRANSLATOR FOR ULTRASONIC IMAGING PROBES, AND METHODS OF USING SAME

(75) Inventors: William E. Webler, Costa Mesa, CA (US); Mark S. Buhr, Newport Beach, CA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/138,477

(22) Filed: May 3, 2002

(65) Prior Publication Data

US 2002/0143255 A1 Oct. 3, 2002

Related U.S. Application Data

(63) Continuation of application No. 09/794,543, filed on Feb. 26, 2001, now Pat. No. 6,409,672, which is a continuation of application No. 09/397,836, filed on Sep. 16, 1999, now Pat. No. 6,193,736, which is a continuation of application No. 09/040,058, filed on Mar. 17, 1998, now Pat. No. 6,013,030, which is a continuation of application No. 08/747,773, filed on Nov. 13, 1996, now Pat. No. 5,759,153, which is a continuation of application No. 08/573,507, filed on Dec. 12, 1995, now Pat. No. 5,592,942, which is a continuation of application No. 08/285,969, filed on Aug. 4, 1994, now Pat. No. 5,485,846, which is a continuation of application No. 07/906,311, filed on Jun. 30, 1992, now Pat. No. 5,361,768.

(51) Int. Cl.[7] ................................................. A61B 8/12

(52) U.S. Cl. ........................................ 600/467; 600/471

(58) Field of Search ........................... 600/444–448, 600/463, 466–467, 471; 606/159, 169

(56) References Cited

U.S. PATENT DOCUMENTS

| 4,679,551 A | 7/1987 | Anthony .................... 128/67 |
| 4,708,125 A | 11/1987 | Miketic et al. ............... 128/4 |
| 4,753,248 A | 6/1988 | Engler et al. ............... 128/736 |

(List continued on next page.)

FOREIGN PATENT DOCUMENTS

| EP | 0 212 225 | 7/1986 |
| WO | WO 90/02520 | 3/1990 |
| WO | WO 90/13259 | 11/1990 |
| WO | WO 90/03095 | 3/1992 |
| WO | 9203095 | 3/1992 |

*Primary Examiner*—Francis J. Jaworski
(74) *Attorney, Agent, or Firm*—Orrick, Herrington & Sutcliffe LLP

(57) ABSTRACT

A longitudinal position translator includes a probe drive module and a linear translation module. The probe drive module is coupled operatively to an ultrasonic imaging probe assembly having a distally located ultrasound transducer subassembly in such a manner that longitudinal shifting of the transducer subassembly may be effected. The probe drive module is preferably mounted to the linear translation unit so as to be moveable between a condition whereby longitudinal shifting of the transducer subassembly can be conducted either manually or automatically. When in the automatically-operable condition, the probe drive module will be engaged with a motor-driven screw associated with the linear translation module so as to cause the probe drive module to be longitudinally displaced at a constant motor-driven rate. In this manner, the distally located ultrasound transducer is longitudinally shifted during an ultrasound scan of surrounding intravascular (or other) tissue to thereby allow axially-spaced 360 data sample "slices" of the surrounding tissue to be obtained. The data samples may then be reconstructed into a three-dimensional or other two-dimensional representations of the scanned vessel to assist in diagnosis.

13 Claims, 6 Drawing Sheets

U.S. PATENT DOCUMENTS

| | | | | |
|---|---|---|---|---|
| 4,771,774 A | | 9/1988 | Simpson et al. .............. 128/305 |
| 4,794,931 A | | 1/1989 | Yock .......................... 128/660 |
| 4,802,487 A | | 2/1989 | Martin et al. ............... 128/662 |
| 4,815,661 A | | 3/1989 | Anthony ................. 239/102.2 |
| 4,926,858 A | * | 5/1990 | Gifford, III et al. ......... 606/159 |
| 4,936,845 A | * | 6/1990 | Stevens ....................... 606/159 |
| 4,951,667 A | | 8/1990 | Crowley ..................... 128/662 |
| 4,951,677 A | | 8/1990 | Crowley et al. ....... 128/662.06 |
| 5,000,185 A | | 3/1991 | Yock .......................... 128/662 |
| 5,030,201 A | | 7/1991 | Polestrant .................... 604/22 |
| 5,105,819 A | | 4/1992 | Wollschlager .............. 128/662 |
| 5,107,844 A | | 4/1992 | Kami et al. ................. 128/662 |
| 5,115,814 A | | 5/1992 | Griffith et al. .............. 128/662 |
| 5,125,410 A | | 6/1992 | Misono et al. .............. 128/662 |
| 5,178,148 A | | 1/1993 | Lacoste et al. ............. 128/662 |
| 5,195,954 A | * | 3/1993 | Schnepp-Pesch et al. ..... 604/22 |
| 5,211,176 A | | 5/1993 | Ishiguro et al. ............. 600/463 |
| 5,255,681 A | | 10/1993 | Ishimura et al. ............ 600/443 |
| 5,295,486 A | | 3/1994 | Wollschlager et al. . 128/661.01 |
| 5,336,167 A | * | 8/1994 | Sullivan et al. ................ 604/22 |
| 5,361,768 A | | 11/1994 | Webler et al. .............. 600/463 |
| 5,421,338 A | | 6/1995 | Crowley et al. ........ 128/660.03 |
| 5,485,846 A | | 1/1996 | Webler et al. .............. 600/463 |
| 5,592,942 A | | 1/1997 | Webler et al. .............. 600/463 |
| 5,759,153 A | | 6/1998 | Webler et al. .............. 600/445 |
| 6,013,030 A | | 1/2000 | Webler et al. .............. 600/437 |
| 6,193,736 B1 | | 2/2001 | Webler et al. .............. 606/171 |

* cited by examiner

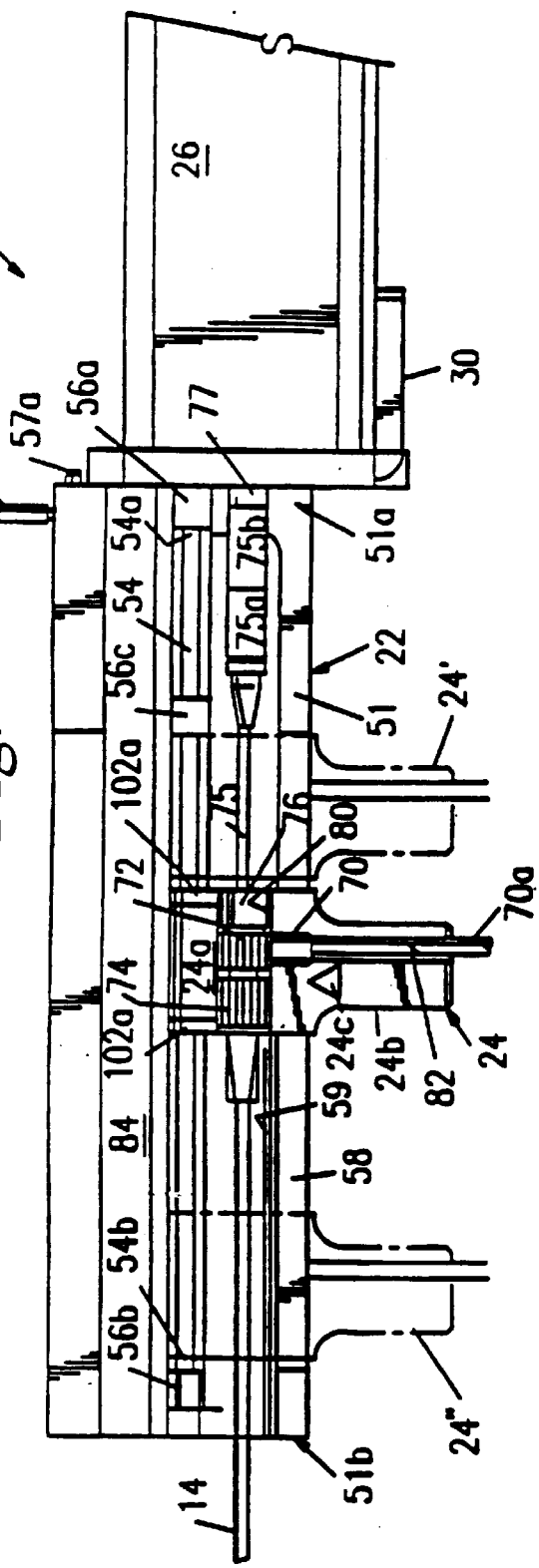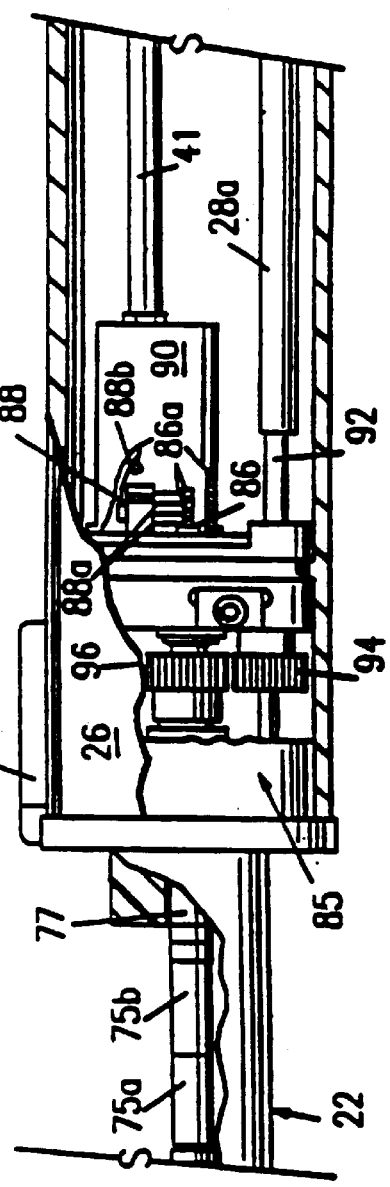

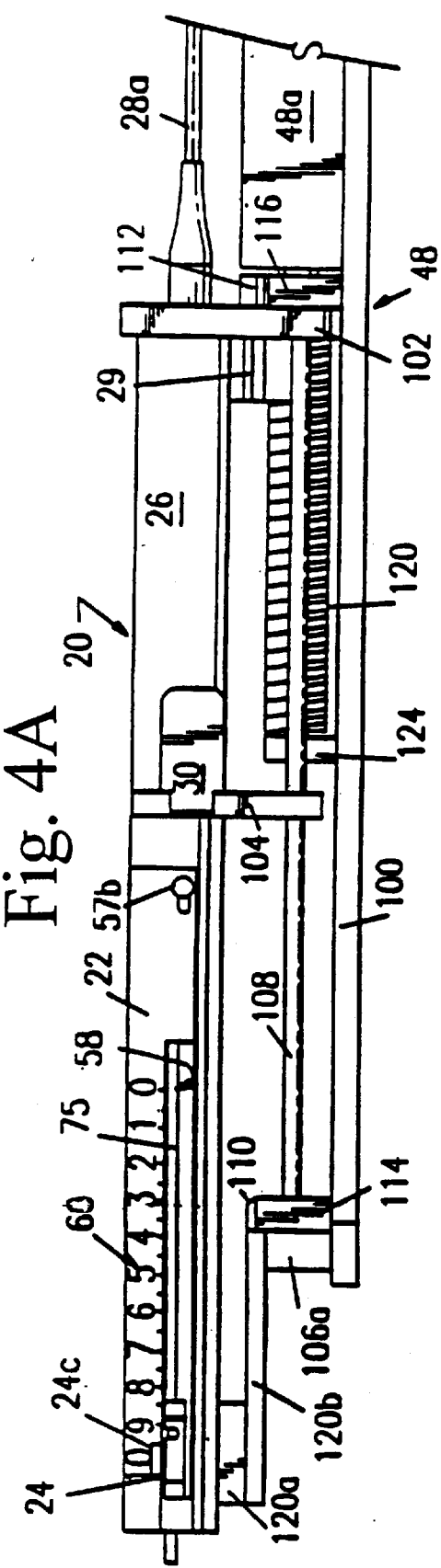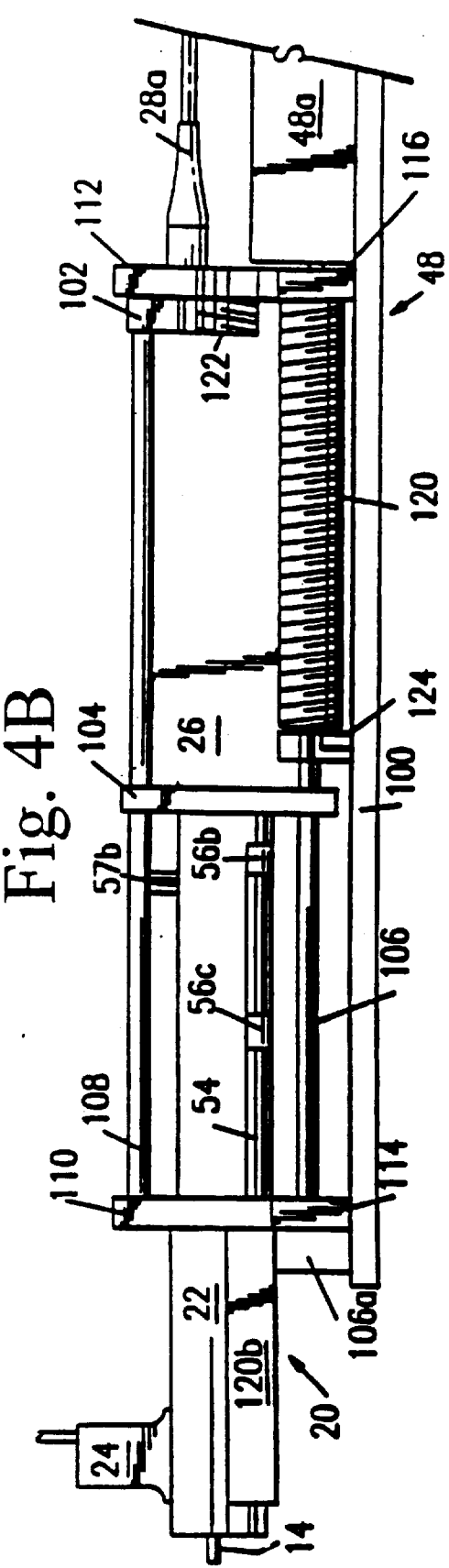

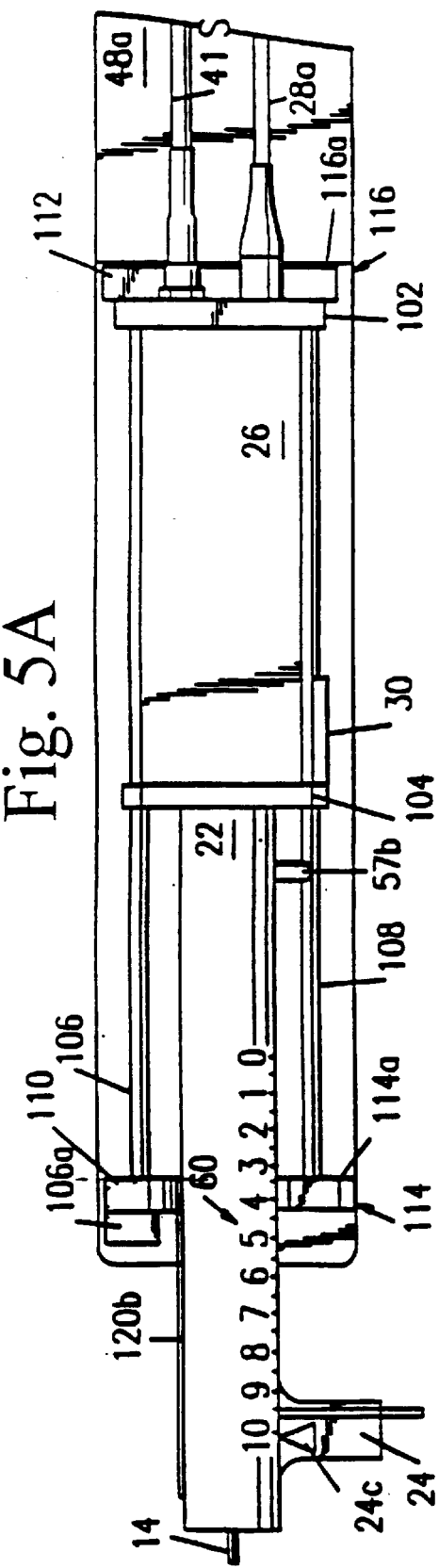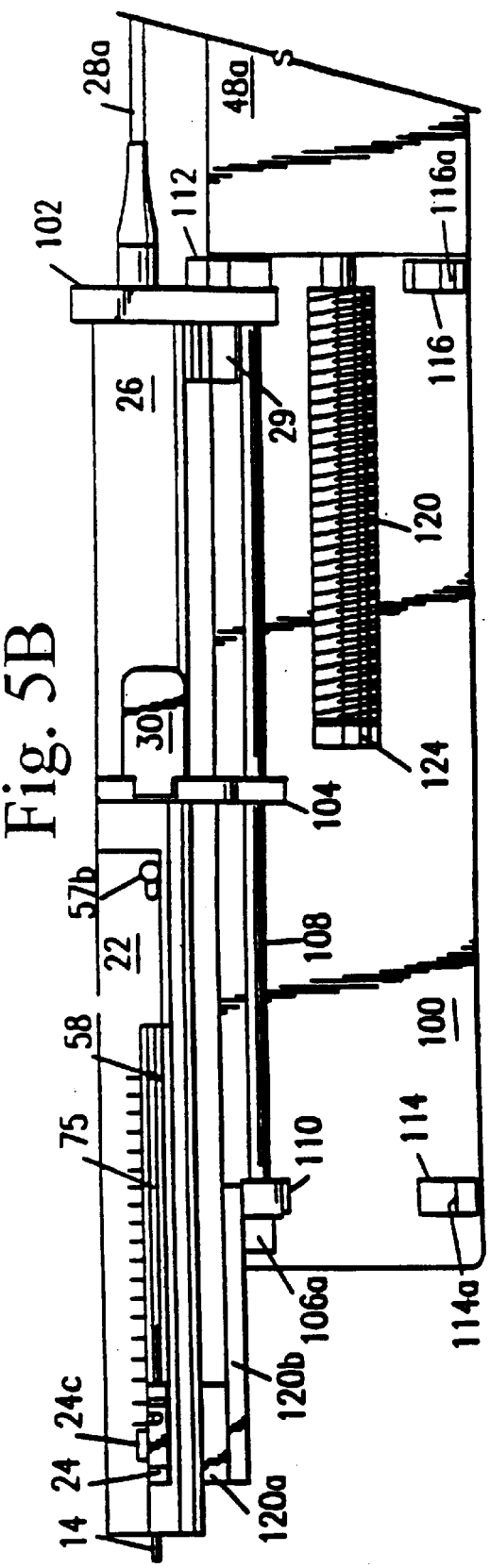

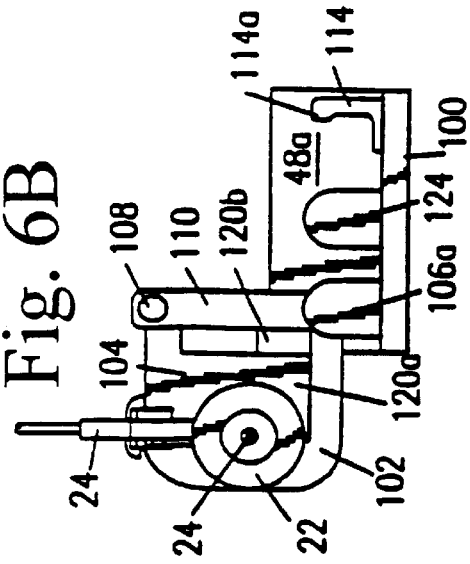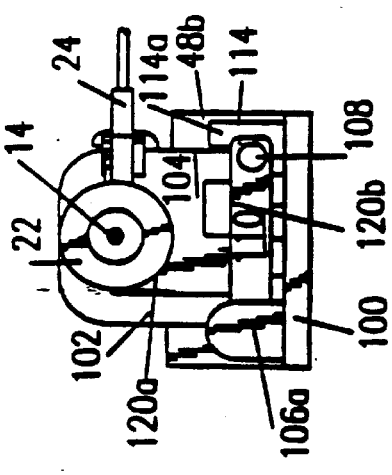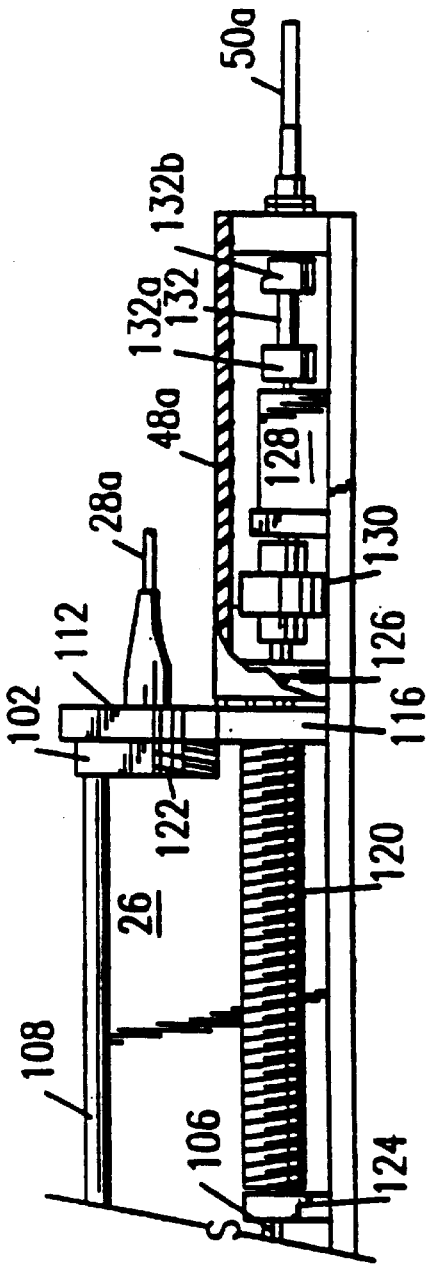

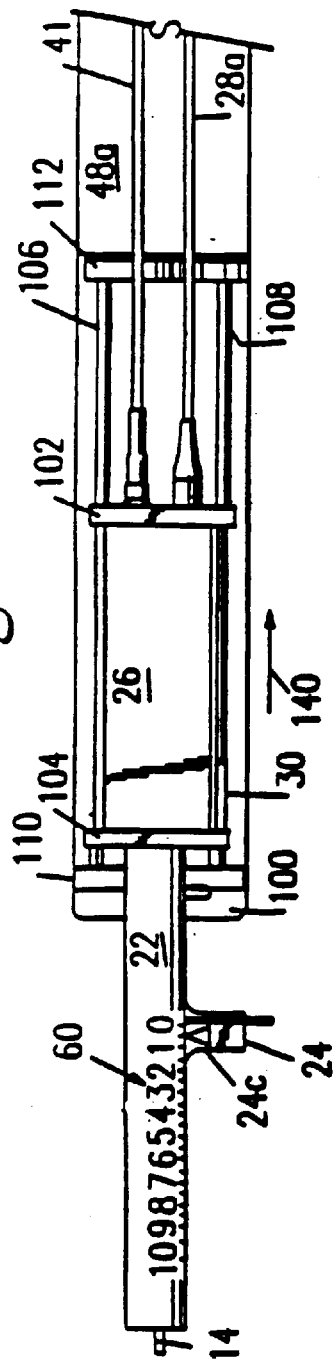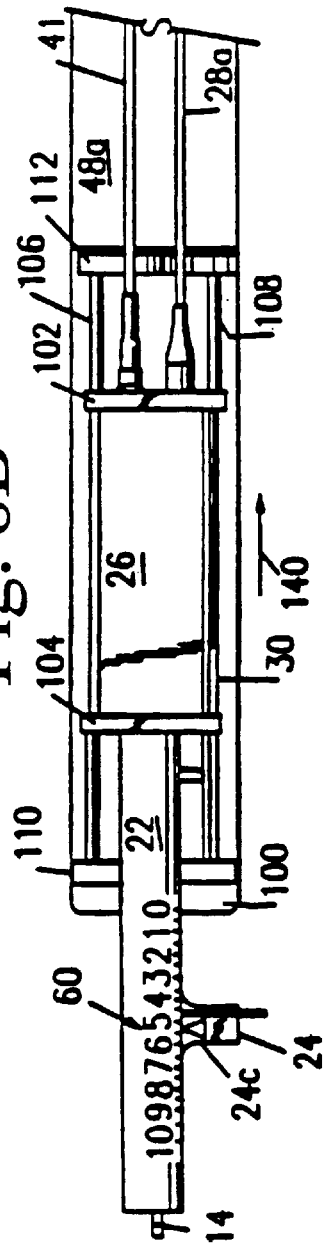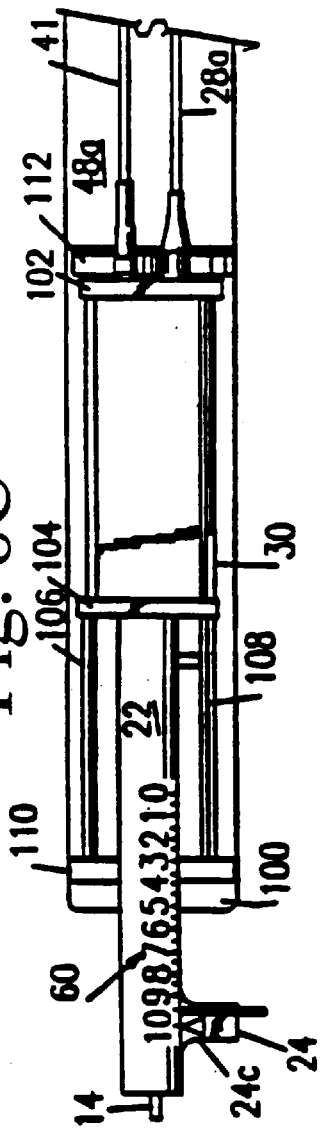

AUTOMATED LONGITUDINAL POSITION TRANSLATOR FOR ULTRASONIC IMAGING PROBES, AND METHODS OF USING SAME

CROSS-REFERENCE TO RELATED PATENTS AND APPLICATIONS

This is a continuation of U.S. application Ser. No. 09/794,543, filed Feb. 26, 2001, now U.S. Pat. No. 6,409,672 which is a continuation of U.S. application Ser. No. 09/397,836, filed Sep. 16, 1999, now U.S. Pat. No. 6,193,736, which is a continuation of U.S. application Ser. No. 09/040,058, filed Mar. 17, 1998, now U.S. Pat. No. 6,013,030, which is a continuation of U.S. application Ser. No. 08/747,773, filed Nov. 13, 1996, now U.S. Pat. No. 5,759,153 which is a continuation of U.S. application Ser. No. 08/573,507, filed Dec. 12, 1995, now U.S. Pat. No. 5,592,942, which is a continuation of U.S. application Ser. No. 08/285,969, filed Aug. 4, 1994, now U.S. Pat. No. 5,485,846, which is a continuation of U.S. application Ser. No. 07/906,311, filed Jun. 30, 1992, now U.S. Pat. No. 5,361,768, which are expressly incorporated herein by reference in their entirety.

FIELD OF INVENTION

The present invention generally relates to elongate probe assemblies of sufficiently miniaturized dimensions so as to be capable of navigating tortuous paths within a patient's organs and/or vessels. In preferred forms, the present invention is embodied in automated units which are connectable to a probe assembly having a distally located ultrasound transducer subassembly which enables the transducer subassembly to be positioned accurately by an attending physician and then translated longitudinally (relative to the axis of the elongate probe assembly) within the patient under automated control.

BACKGROUND OF THE INVENTION

I. Introductory Background Information

Probe assemblies having therapeutic and/or diagnostic capabilities are being increasingly utilized by the medical community as an aid to treatment and/or diagnosis of intravascular and other organ ailments. In this regard, U.S. Pat. No. 5,115,814 discloses an intravascular probe assembly with a distally located ultrasonic imaging probe element which is positionable relative to intravascular sites. Operation of the ultrasonic element in conjunction with associated electronic components generates visible images that aid an attending physician in his or her treatment of a patient's vascular ailments. Thus, a physician may view in real (or essentially near real) time intravascular images generated by the ultrasonic imaging probe element to locate and identify intravascular abnormalities that may be present and thereby prescribe the appropriate treatment and/or therapy.

The need to position accurately a distally located operative probe element relative to an intravascular site using any therapeutic and/or diagnostic probe assembly is important so that the attending physician can confidently determine the location of any abnormalities within the patient's intravascular system. Accurate intravascular position information for the probe assembly will also enable the physician to later replicate probe positions that may be needed for subsequent therapeutic and/or diagnostic procedures. For example, to enable the physician to administer a prescribed treatment regimen over time and/or to later monitor the effects of earlier therapeutic procedures.

Recently ultrasonic imaging using computer-assisted reconstruction algorithms has enabled physicians to view a representation of the patient's interior intravascular structures in two or three dimensions (i.e., so-called three dimensional or longitudinal view reconstruction). In this connection, the current image reconstruction algorithms employ data-averaging techniques which assume that the intravascular structure between an adjacent pair of data samples will simply be an average of each such data sample. Thus, the algorithms use graphical "fill in" techniques to depict a selected section of a patient's vascular system under investigation. Of course, if data samples are not sufficiently closely spaced, then lesions and/or other vessel abnormalities may in fact remain undetected (i.e., since they might lie between a pair of data samples and thereby be "masked" by the image reconstruction algorithms mentioned previously).

In practice, it is quite difficult for conventional ultrasonic imaging probes to obtain sufficiently closely spaced data samples of a section of a patient's vascular system under investigation since the reconstruction algorithms currently available depend upon the software's ability to process precisely longitudinally separated data samples. In this regard, conventional intravascular imaging systems depend upon manual longitudinal translation of the distally located ultrasound imaging probe element by an attending physician. Even with the most skilled physician, it is practically impossible manually to exercise constant rate longitudinal translation of the ultrasound imaging probe (which thereby provides for a precisely known separation distance between adjacent data samples). In addition, with manual translation, the physician must manipulate the translation device while observing the conventional two dimensional sectional images. This division of the physician's attention and difficulty in providing a sufficiently slow constant translation rate can result in some diagnostic information being missed. In order to minimize the risk that diagnostic information is missed, then it is necessary to devote more time to conducting the actual imaging scan which may be stressful to the patient.

Thus, what has been needed in this art, is an ultrasound imaging probe assembly which is capable of being translated longitudinally within a section of a patient's vascular system at a precise constant rate. Such an ability would enable a series of corresponding precisely separated data samples to be obtained thereby minimizing (if not eliminating) distorted and/or inaccurate reconstructions of the ultrasonically scanned vessel section (i.e., since a greater number of more closely spaced data samples could reliably be obtained). Also, such an assembly could be operated in a "hands-off" manner which would then allow the physician to devote his attention entirely to the real time images with the assurance that all sections of the vessel were displayed. In terms of reconstruction, the ultrasound imaging probe could be removed immediately and the physician could interrogate the images or their alternative reconstructions on a near real time basis. Such a feature is especially important during coronary diagnostic imaging since minimal time would be needed to obtain reliable imaging while the blood flow through the vessels is blocked by the probe assembly. It is therefore towards fulfilling such needs that the present invention is directed.

II. Information Disclosure Statement

One prior proposal for effecting longitudinal movements of a distally located operative element associated with an elongate probe assembly is disclosed in U.S. Pat. No. 4,771,774 issued to John B. Simpson et al on Sep. 20, 1988 (hereinafter "Simpson et al '774"). The device disclosed in Simpson et al '774 includes a self-contained motor drive unit for rotating a distally located cutter element via a flexible drive cable with manual means to effect relative longitudinal movements of the rotating cutter element.

More specifically, in Simpson et al '774, the proximal end of a flexible drive cable is slidably coupled to a hollow extension rotary drive shaft with a splined shaft. The hollow extension drive shaft is, in turn, coupled to a motor, whereas the splined shaft cooperates with a manually operated slide member. Sliding movements of the slide member relative to the motor drive unit housing translate into direct longitudinal movements of the flexible drive cable, and hence the distally located cutter element. In brief, this arrangement does not appear to allow for automated longitudinal movements of the distally located probe element.

SUMMARY OF THE INVENTION

The longitudinal position translator of the present invention is especially adapted for use with an intravascular probe assembly of type disclosed in the above-mentioned U.S. Pat. No. 5,115,814 (incorporated fully by reference hereinto). That is, the preferred intravascular probe assembly with which the position translator of the present invention may be used will include a flexible guide sheath introduced along a tortuous path of a patient's vascular system, and a rotatable probe element (preferably an ultrasonic imaging probe) which is operatively introduced into the lumen of the guide sheath. Of course, the position translator of the present invention may be modified easily to accommodate less complex one-piece ultrasonic probe assemblies. Rotational movements supplied by a patient-external motor are transferred to a distally located transducer subassembly by means of a flexible torque cable which extends through the guide sheath.

As is described more completely in U.S. Pat. No. 5,115,814, the interior of the guide sheath provides a bearing surface against which the probe element rotates. This bearing surface supports the probe element during its rotation so that virtually no "play" is present—that is, so that the probe element rotates essentially coaxially relative to the vascular vessel undergoing therapy and/or investigation. The probe element is also longitudinally (i.e. axially) movable so that axial-spaced 360.degree. data sample "slices" of the patient's vascular vessel wall can be imaged.

The automated longitudinal position translator of the present invention generally includes a probe drive module and a linear translation module. The probe drive module is most preferably embodied in an elongate barrel-shaped housing structure having a manual positioning lever capable of reciprocal movements between advanced and retracted positions. The lever captures a proximal end of the guide sheath within which a probe element is disposed. A flexible torque cable connects the transducer subassembly at the distal end of the probe element to a drive shaft which is driven, in the preferred embodiment, by a precision rate-controlled motor located in a separate fixed base unit. Preferably, the housing is hinged in a "clamshell" fashion to more easily facilitate electrical and mechanical coupling of the intravascular probe assembly. The lever may be eliminated when using less complex one-piece ultrasonic probe assemblies or modified so as to capture the guide catheter or introducer.

The linear translation module supports the probe drive module. In addition, the linear translation module is coupled operatively to the probe drive module so as to allow for relative hinged movements thereby and thus permit the probe drive module to be moved between a manually-operable condition (whereby the probe drive module is disengaged from the longitudinal drive subassembly associated with the linear translation module to thereby allow a physician to exercise manual control over the longitudinal positioning of the probe element) and an automated condition (whereby the probe drive module is operatively engaged with the linear translation module so that automated longitudinal position control over the probe element can be exercised).

In use, the ultrasound imaging probe will be physically positioned by an attending physician within a section of a patient's vascular system under investigation using conventional fluoroscopic positioning techniques. Thereafter, the proximal portion of the probe and guide sheath assembly will be coupled to the probe drive module. The probe drive module can then be employed to either manually or automatically translate the imaging probe element longitudinally within the section of the patient's vascular system under investigation during an ultrasonic imaging scan of the same as may be desired by the attending physician by moving the probe drive module between its manual and automated conditions, respectively. The present invention thus allows the distally located probe element to be rotated, while simultaneously providing the attending physician with the capability of longitudinally translating the probe element at a constant automated translation rate to thereby obtain reliable data samples representative of longitudinally spaced-apart data "slices" of the patient's vascular section under investigation. These data "slices" may then be reconstructed using conventional computer-assisted algorithms to present the entire section of the patient's vascular system under investigation in a more informative "two-dimensional" longitudinal or "three-dimensional" image display on a CRT (or other) monitor. The physician can thus manipulate the image orientation or two-dimensional sectional plane of the vascular section electronically and thereby achieve a more informative representation of the condition of the patient's vascular section under investigation.

In its preferred embodiment, the linear position translator provides for automated translation of the imaging probe from a distal location to a proximal location only. Thus, the imaging probe would not be advanced under automated control into the guide sheath. Such a preferred functional attribute eliminates the need for sophisticated sensor and control systems to sense and stop probe advancement should it encounter a "kink" or non-negotiable sharp bend in the guiding sheath. Furthermore, during probe withdrawal (i.e., distal to proximal motion), the guide sheath is supported by the probe and may not "kink". Also, since the probe has already negotiated all bends during its initial manual distal advancement, the attending physician is assured that the bends are in fact negotiable by the probe upon its withdrawal through that same path. Thus, although the preferred embodiment contemplates automated longitudinal translation in a proximal direction, it is likewise preferred that the attending physician advance the probe in a distal direction manually so that the physician may use his or her experience with the catheters and the tactile sensations to judge when an obstruction has been encountered.

Further features and advantages of the present invention will become more clear after careful consideration is given to the following detailed description of presently preferred exemplary embodiments.

BRIEF DESCRIPTION OF THE ACCOMPANYING DRAWINGS

Reference will hereinafter be made to the accompanying drawings wherein like reference numerals throughout the various FIGURES denote like structural elements, and wherein;

FIG. 2 is a top plan view of the probe drive module employed with the longitudinal position translator according to the present invention showing the housing thereof in an opened state;

FIG. 3 is a side elevation view, partly in section, of the probe drive module shown in FIG. 2;

FIGS. 4A and 4B are each side elevation views of the longitudinal position translator according to the present invention in its automated and manual conditions, respectively;

FIGS. 5A and 5B are each top plan views of the longitudinal position translator according to the present invention in its automated and manual conditions, respectively;

FIGS. 6A and 6B are each front end elevational views of the longitudinal position translator according to the present invention in its automated and manual conditions, respectively;

FIG. 7 is a partial side elevational view which is also partly in section of the longitudinal position translator according to the present invention; and FIGS. 8A–8C are top plan views of the longitudinal position translator according to this invention which schematically depict a preferred mode of automated operation.

DETAILED DESCRIPTION OF THE PREFERRED EXEMPLARY EMBODIMENTS

Figure 1:
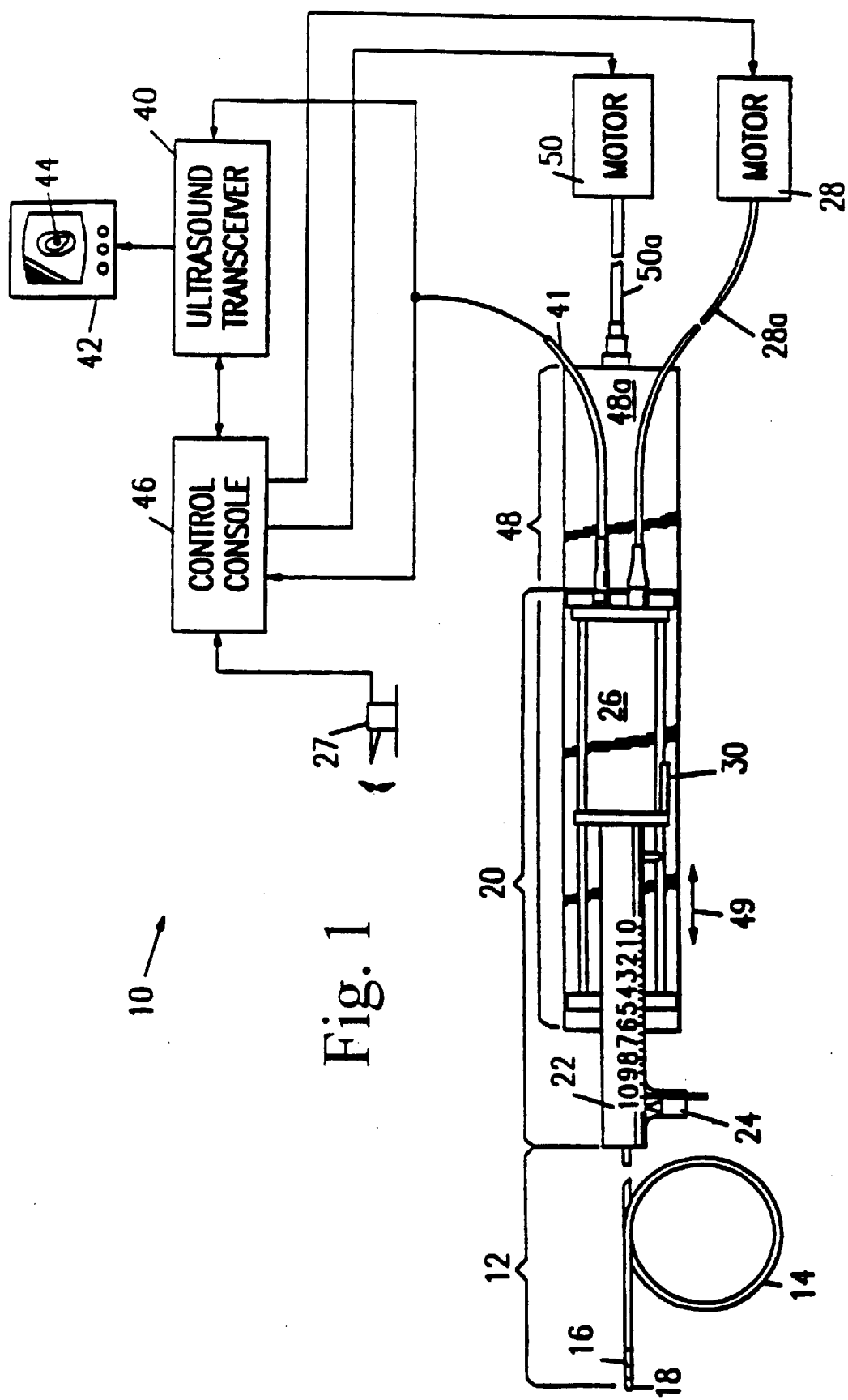
FIG. 1 is a schematic view of an ultrasonic imaging system that includes an automated longitudinal position translator according to the present invention.

A schematic diagram of an exemplary ultrasound imaging system 10 is shown in accompanying FIG. 1. System 10 generally includes an ultrasound imaging probe assembly 12 having a guide sheath 14 and a distally located ultrasound imaging probe element 16 inserted into the lumen of guide sheath 14, the probe element 16 being depicted in FIG. 1 as being visible through the guide sheath's transparent wall. The ultrasonic imaging probe assembly 12 preferably embodies those features more fully described in the above-identified U.S. Pat. No. 5,115,814.

The overall length of the imaging probe assembly 12 is suitable for the desired diagnostic and/or therapeutic intravascular procedure. For example, the overall length of the probe assembly 12 may be shorter for direct (e.g., arteriotomy) insertions as compared to the length of the probe assembly 12 needed for percutaneous distal insertions (e.g., via the femoral artery). A representative length of the imaging probe assembly 12 is therefore shown in the accompanying drawings for clarity of presentation.

The terminal end of the guide sheath 14 preferably carries a radiopaque marker band 18 formed of gold or other fluoroscopically visible material. The marker band 18 allows the attending physician to monitor the progress and position of the guide sheath 14 during intravascular insertions using standard fluoroscopic imaging techniques.

The proximal end of the imaging probe assembly 12 is received within a probe drive module 20. In essence, the probe drive module 20 includes a distally open-ended and longitudinally barrel-shaped housing 22, and a positioning lever 24 which captures the proximal end of the guide sheath 14. The proximal end of the ultrasound imaging probe element 16 is mechanically and electrically connected to the probe drive module 20. Longitudinal reciprocal movements of the positioning lever 24 relative to the housing 22 will thus in turn effect relative longitudinal displacements of the distal end of the probe element 16 within the guide sheath 14 relative to the longitudinal axis of the probe assembly 12.

The probe drive module 20 also includes a drive unit 26 fixedly connected proximal to the housing 22 and contains the structures which supply mechanical rotation and electrical signals to the probe element 16. In the preferred embodiment, mechanical rotation of the probe element 16 is provided by a separate precision motor 28 associated with a base unit (not shown) and operatively coupled to the probe drive module 20 via a flexible drive cable 28a. It is entirely conceivable, however, that the drive unit 26 could be sized so as to accommodate the motor 28.

The drive unit 26 is most preferably configured so that the attending physician may comfortable grasp its exterior with one hand while the probe drive module 20 is in its manual condition. The drive unit 26 thus forms a handle which allows the physician to manually manipulate the relative position between the housing 22 and the positioning lever 24 thereby responsively permitting manual longitudinal movements to be imparted to the probe element 16. A thumb/finger switch 30 may thus be manually depressed to allow the physician to selectively operate the drive unit 26 and thereby rotate the ultrasonic imaging probe element 16 when it is desired to conduct an ultrasonic imaging scan. Electrical connection between the switch 30 and the control console 46 is made via I/O cabling 41.

During rotation, electrical communication is established between the transducer subassembly in the distal end of the ultrasonic imaging probe element 16 and the ultrasound transceiver 40 via patient-internal electrical coaxial cabling (not shown) within the probe element 16, drive unit 26 and electrical patient-external I/O cabling 41. The ultrasound transceiver 40 produces a pulse signal (of desired magnitude and shape) which is applied via the electrical cabling 41 to an electroacoustic transducer associated with the distal end of the probe element 16. The transceiver 40 also performs conventional signal processing operations (e.g., amplification, noise reduction and the like) on electrical signals generated by the electromechanical excitation of the transducer within the probe element 16 (i.e., signals generated by the transducer in response to receiving acoustic echo waves).

These signals are further processed digitally via known display algorithms (e.g., conventional PPI (radar) algorithms) and are then supplied as input to a CRT monitor 42 (or any other equivalent display device) so as to generate an ultrasound image 44 of desired format representative of the vascular structures reflecting ultrasonic energy toward the transducer within the distal end of the probe element 16. A control console 46 may be employed by the attending physician so as to select the desired operational parameters of the ultrasound transceiver 40 and/or the display format of the image 44 on the CRT 42, for example.

The probe drive module 20 is operatively coupled to and supported by the linear translation module 48 so as to allow for reciprocal rectilinear movements of the housing 22/drive unit 26 relative to both the linear translation module 48 and the positioning arm 24 which collectively remain in a fixed position as will be described in greater detail below. As will also be described in greater detail below, the probe drive module 20 is mounted for hinged movements relative to the linear translation module 48 between a manually-operable condition (whereby the probe drive module 20 is operatively disengaged from the motor driven translator associated with the linear translation module 48) and a automatically-operable condition (whereby the probe drive module 20 is operatively engaged with the motor driven translator associated with the linear translation module 48).

The linear translation module 48 includes a proximal housing 48a which contains appropriate speed-reducers, drive shafts and associated couplings to be described below in connection with FIG. 7. Suffice it to say here, however, that driven power is provided to the structures internally of housing 48a by a separated precision motor 50 associated with a system base unit (not shown) which is coupled operatively to the structures internally of housing 48a via a flexible drive shaft 50a. Again, it is entirely conceivable that the housing 48a of the linear translation module 48 could be sized and configured so as to accomodate the motor 50. Automated operation of the motor 50 (and hence the linear translation module 48) may be accomplished through the selection of appropriate operation parameters by the attending physician via control console 46. Operation of both the linear translation module 48 and the probe drive module 20 may be initiated by depressing the foot-switch 27.

The exemplary probe drive module 20 which is employed in the present invention is perhaps more clearly depicted in accompanying FIGS. 2 and 3. As is seen, the housing 22 is collectively formed of a pair of elongate lower and upper housing sections 51, 52, respectively, which are coupled to one another along adjacent longitudinal edges in a clamshell-hinged arrangement via hinge pin 54.

It will be noticed with particular reference to FIG. 2 that the proximal and distal ends 54a, 54b of pin 54 are rigidly fixed to the proximal and distal ends 51a, 51b of housing section 51, respectively, while the housing section 52 is pivotally coupled to the pin 54 (and hence the housing section 51) by means of proximal and distal and intermediate pivot sleeves 56a, 56b and 56c, respectively. The housing sections 51, 52 are maintained in their closed state (i.e., as shown in FIGS. 4A through 5B) by means of a spring-loaded detent 57a (see FIG. 2) which may be moved into and out of an aperture (not shown) formed in the housing section 51 via operating lever 57b.

The positioning lever 24 is oriented transversely relative to the elongate axis of housing 22. In this regard, the lever 24 includes a sleeve end 24a which is coupled to the pivot pin 54 to allow reciprocal longitudinal and pivotal movements of the lever 24 to occur relative to the longitudinal axis of pin 54. The opposite end 24b of lever 24 extends radially outwardly from the housing 22.

The housing 22 defines an elongate slot 58 when the housing sections 51, 52 are in a closed state (i.e., as depicted in FIG. 1). The slot 58 allows the positioning lever 24 to be manually moved along the longitudinal axis of pin 54 during use (i.e., when the housing sections 51, 52 are in a closed state) between retracted and extended positions (shown respectively by phantom line representations 24' and 24" in FIG. 2). The retracted position 24' of lever 24 is established by a distal face of a pivot sleeve 56c integral with the housing section 52 and pivotally coupled to pin 54 in a manner similar to pivot sleeves 56a and 56b. On the other hand, the extended position 24" of lever 24 is established by a proximal face of pivot sleeve 56b.

The lever 24 is supported by a concave inner surface 59 formed in the housing section 51 when the housing sections 51 and 52 are in a closed state. The inner surface 59 provides a bearing surface against which the lever 24 slides during the latter's movement between its retracted and extended positions 24' and 24", respectively.

A scale 60 (see FIGS. 4A and 5A) preferably is provided on the housing 22. A pointer 24c associated with the lever 24 may be aligned with the scale 60 to provide an attending physician with information regarding the position of probe element 16 relative to its most distal position within the guide sheath 14. That is, longitudinal movement of lever 24 an incremental distance (as measured by pointer 24c and the scale 60) will effect movement of the probe element 16 relative to its most distal position within the guide sheath's distal end by that same incremental dimension.

Accompanying FIG. 2 also more clearly shows the cooperative engagement between positioning lever 24 and the proximal end of guide sheath 14. In this regard, it will be noted that the proximal end of guide sheath 14 includes a side-arm port 70 which extends generally transverse to the longitudinal axis of guide sheath 14. Side-arm port 70 includes a conventional Leur-type locking cap 72 that is coupled coaxially to a similar locking cap 74 associated with the proximal end of guide sheath 14. Side-arm port 70 is thus in fluid-communication with the lumen of guide sheath 14 so that saline solution, for example, may be introduced via side-arm tubing 70a.

A shaft extension 75 of probe element 16 and electrical cabling coaxially carried thereby are mechanically and electrically coupled to the output shaft 77 of the probe drive module 20 via coaxial cable couplings 75a and 75b. It will be appreciated that coaxial cabling within the flexible torque cable portion of probe element 16 (not shown) will rotate with it as a unit during operation, but that the electrical I/O signals will be transferred to transceiver 40 by means of couplings 75a and 75b. The manner in which the separate electrical I/O path (represented by cable 41—see FIG. 1) and mechanical input path (represented by the flexible drive shaft 28a—see FIG. 1) are combined into a common electrical/mechanical output path (represented by output shaft 77) will be explained in greater detail with reference to FIG. 3.

The shaft extension 75 is preferably fabricated from a length of conventional stainless steel hypodermic tube and is rigidly coupled at its distal end to a flexible torque cable (not shown). As mentioned briefly above, the torque cable extends the length of the guide sheath 14 and is connected at its distal end to a transducer subassembly in the distal end of the probe element 16. The torque cable thereby transfers the rotational motion imparted via the motor to shaft extension 75 of the probe element 16 causing the transducer subassembly to similarly rotate within the lumen of the guide sheath 14 near the guide sheath's distal end, as well as to be longitudinally shifted within guide sheath 14 via manipulation of the relative position of the arm 24.

The shaft extension 75 extends through an end cap 76 which is coupled coaxially to locking caps 72 and 74. End cap 76 houses a synthetic resin bearing element (not shown) which serves as a proximal rotational bearing for the shaft 75, and also serves to seal the proximal end of guide sheath 14 against fluid (e.g., saline liquid) leakage.

Lever 24 defines a pair of mutually transverse concave cradle surfaces 80 and 82. The longitudinal dimension of cradle surface 80 is oriented parallel to the longitudinal dimension of housing 22, whereas cradle surface 82 (which is joined at one of its ends to the cradle surface 80) is oriented transverse to the longitudinal dimension of housing 22 (i.e., since it is traverse to cradle surface 80).

Cradle surface 80 is sized and configured so as to accommodate an exterior surface portion of coaxially locked caps 72, 74 and 76. Cradle surface 82, on the other hand, is sized and configured to accept side-arm port 70 and side-arm tubing 70a extending therefrom. An axially extending inner concave surface 84 is defined in housing section 52 and, like cradle surface 82, is sized and configured so as to accept an exterior portion of locking caps 72, 74 and 76.

When housing sections 51 and 52 are in a closed state, caps 72, 74 and 76 will be enveloped by housing 22. More specifically, inner concave surface 84 will positionally restrain caps 72, 74 and 76 within cradle surface 80 when housing sections 51 and 52 are closed. Since side-arm port 70 will likewise be positionally restrained within cradle surface 82 when housing sections 51, 52 are closed, caps 72, 74 and 76 will be moved longitudinally as a unit with position lever 24. That is, longitudinal movements of lever arm 24 between its retracted and extended positions will cause the proximal end of guide sheath 14 (i.e., coaxially mounted caps 72, 74 and 76) to be longitudinally moved relative to the longitudinally stationary (but axially rotatable) shaft extension 75. In such a manner, the proximal end of guide sheath 14 will be moved closer to and farther from the open distal end of housing 22.

As can be seen in FIG. 3, the interior of the drive unit 26 is hollow to house electrical/mechanical coupling assembly 85. Electrical/mechanical coupling 85 combines an electrical input path—represented by coaxial I/O cable 41 which establishes electrical communication with transceiver 40—and a mechanical input path—represented by flexible drive shaft 28a associated with motor 28 (see FIG. 1) into a common coaxial output shaft 77.

Output shaft 77 is rotatably held within bearing block 86 and includes a rearwardly extending rotatable tail portion carrying a number of electrical slip-rings 86a. Electrical communication between the slip-rings 86a and coupling 75b is established by a length of coaxial cable (not shown) housed within the output shaft 77. Stationary brushes 88a in sliding electrical contact with respective ones of the slip-rings 86a are associated with a brush block 88. Lead wires 88b are, in turn, coupled electrically at one end to brush block 88 (and hence to coaxial connector 75a via brushes 88a and slip-rings 86a), and at the other end to coaxial I/O cable 41 via a ferrite coil transformer (not shown). Slip-rings 86a, brushes 88a, brush block 88, lead wires 88b, and ferrite core transformer (not shown) are housed within a common electrically shielded enclosure 90.

The mechanical input path generally represented by flexible drive shaft 28a is coupled operatively to one end of a rigid rotatable drive shaft 92 carrying a drive gear 94 at its other end. Drive gear 94 is, in turn, meshed with a gear 96 carried by output shaft 77. Upon rotation of drive shaft 92, meshed gears 94, 96 will cause shaft 77 to responsively rotate. Preferably, gears 94 and 96 are in a 1:1 ratio, but other gear sizes (and hence ratios) may be provided if desired.

The probe drive unit 20 is mounted for reciprocal rectilinear movements to the linear translation module 48 as is shown in accompanying FIGS. 4A through 6B. In this regard, the linear translation module includes a base plate 100 which supports the housing 48a and its internal structures (to be described below with reference to FIG. 7). The probe drive module 20 itself includes a longitudinally spaced-apart pair of support flanges 102, 104, each of which is slidably mounted onto a pair of parallel guide rails 106, 108.

The proximal end of guide rail 106 is pivotally connected to the housing 48a while its distal terminal end is pivotally connected to an upright support block 106a. A forward and rearward pair of transverse support arms 110, 112 each having one end rigidly coupled to guide rail 106 and an opposite end rigidly coupled to the guide rail 108. Thus, the support arms 110, 112 are capable of pivoting between a lowered position (e.g., as shown in FIGS. 4A, 5A and 6A) and a raised position (e.g., as shown in FIGS. 4B, 5B and 6B) by virtue of the pivotal guide rail 106 so as to, in turn, pivotally move the probe drive module 20 between its automatically-operable condition and its manually-operable condition, respectively, due to its attachment to the guide rails 106, 108 via support flanges 102, 104.

The ends of each transverse support arm 110, 112 between which the guide rail 108 is fixed are removably captured by upright restraining posts 114, 116, respectively. As is perhaps more clearly shown in FIGS. 6A and 6B, the restraining posts 114, 116 (only restraining post 114 being visible in FIGS. 6A and 6B) are rigidly supported by the base plate 100 and include an inwardly projecting lip 114a, 116a which provide an interference fit with the terminal ends of support arms 110, 112, respectively. In this connection, it is preferred that the restraining posts 114, 116 be formed of a relatively stiff, but resilient plastics material (e.g., nylon, polyacetal or the like) so that when the probe drive unit is moved between its automatically-operable and manually-operable conditions, the posts 114, 116 are capable of yielding somewhat to allow such movement.

The positioning arm 24 of the probe drive unit 20 is fixedly tied to the forward transverse support arm 110 by an upright connector 120a on a longitudinal connector 120b. In this regard, the upper end of upright connector 120a extends through a longitudinal slot on the side of the housing 22 opposite slot 58 and positionally captures the ends of the positioning arm 24 around pin 54. The lower end of the upright connector 120a is connected to the distal end of the horizontally disposed longitudinal connector 120b. The proximal end longitudinal connector 120b is, in turn, rigidly fixed to the transverse support arm 110 by any suitable means (e.g., screws). It will be understood, therefore, that the position of the positioning arm 24 (and hence the guide sheath 14) remains fixed relative to the base 100 of the linear translation module 48 during longitudinal movements of the probe drive module 20 along the guide rails 106 and 108. Thus, the relative position of the patient-internal transducer subassembly at the distal end of the probe element 16 will correspondingly shift the same distance as the probe drive module 20 relative to the patient internal distal end of the guide sheath 14.

Automated longitudinal shifting of the probe drive module 20 (and hence the ultrasonic transducer subassembly at the distal end of the probe element 16) is permitted by the coaction between a longitudinally extending drive screw 120 and a threaded collar portion 122 (see FIGS. 4B and 7) associated with the support flange 102 of the probe drive module 20. The distal and proximal ends of the drive screw 120 are rotatably supported by an upright distal bearing block 124 and an upright proximal bearing block 126 (see FIG. 7), respectively.

As can be seen in FIGS. 4B, 5B, 6B and 7, the threaded collar portion 122 is disengaged from the threads of drive screw 120 when the probe drive module 20 is in its manually-operable condition. As a result, the attending physician may simply manually shift the probe drive module 20 longitudinally along the guide rails 106, 108. When the probe drive module 20 is pivoted into its automatically-operable condition as shown in FIGS. 4A, 5A and 6A, the threads associated with the threaded collar portion 122 will be mateably engaged with the threads of the drive screw 120. As a result, rotation of the drive screw 120 about its longitudinal axis will translate into longitudinal displacement of the probe drive module 20. The threads of the drive screw 120 and the threaded collar portion 122 as well as the rotation direction of the drive screw 120 are most preferably selected so as to effect longitudinal shifting of the probe drive module from the distal end of the drive screw towards the proximal end thereof—i.e., a distal to proximal displacement. However, these parameters could be changed so as to effect a reverse (proximal to distal) displacement of the probe drive unit, if necessary or desired.

The drive screw 120 is coupled operatively to the flexible drive shaft 50a (and hence to the driven output of motor 50) by the structures contained within housing 48a. In this regard, the proximal end of the drive screw is coupled to the output shaft of a speed reducer 128 via a shaft coupling 130. The input to the speed reducer 128 is, in turn, coupled to the flexible drive shaft 50a from a rigid shaft extension member 132 and its associated shaft couplings 132a and 132b. The speed reducer 128 is of a conventional variety which provides a predetermined reduced rotational speed output based on the rotational speed input. Preferably, the motor 50, speed reducer 128 and drive screw 120 are designed so as to effect longitudinal translation of the probe drive unit 20 at a rate of between about 0.25 to 1.0 mm/sec. Of course, other longitudinal translation rates may be provided by varying the parameters of the motor 50, speed reducer 128 and/or drive screw 120.

In use, the attending physician will preposition the guide sheath 14 and imaging probe element 16 associated with the ultrasound imaging probe assembly 12 within the vessel of the patient to be examined using standard fluoroscopic techniques and/or the techniques disclosed in the above-mentioned U.S. Pat. No. 5,115,814. Once the guide sheath 14/imaging probe element 16 have been prepositioned in a region of the patient's vessel which the physician desires to observe, the proximal end of the probe assembly 12 will be coupled to the probe drive module 20 in the manner described above. Thereafter, the physician may conduct an ultrasound scan of the patient's vessel by operating switch 30 to cause high-speed rotation of the transducer subassembly on the distal end of the probe element 16 within the guide sheath 14. Data samples associated with different transverse sections of patient's vessel may then be obtained by the physician manually shifting the probe drive module 20 along the guide rails 106, 108 in the manner described above.

Alternatively, the physician may elect to pivot the probe drive module 20 into its automatically-operable condition and then select automated operation of the same via the control console 46 and foot-switch 27. In such a situation, the probe drive module (and hence the transducer subassembly at the distal end of the probe element 16) will be shifted longitudinally at a constant rate simultaneously with high-speed rotation of the transducer subassembly. In this manner, data samples representing longitudinally spaced-apart 360.degree. "slices" of the patient's interior vessel walls will be accumulated which can then be reconstructed using known algorithms and displayed in "two-dimensional" or "three-dimensional" formats on the monitor 42.

Accompanying FIGS. 8A–8C schematically depict the longitudinal translator according to this invention being operated in an automated manner. In this connection, and as was noted briefly above, the probe drive module 20 is most preferably translated in a distal to proximal direction by means of the linear translation module 48 (i.e., in the direction of arrows 140 in FIGS. 8A and 8B). In FIG. 8A, the probe drive module is shown in a position at the beginning of an automated ultrasonic imaging scan, it being noted that the pointer 24c associated with the positioning arm 24 registers with the zero marking on the scale 60. The physician will then initiate automated ultrasonic scanning via the foot-switch 27 which causes the probe drive unit 20 to be displaced proximally (arrow 140) at a constant rate as shown in FIG. 8B. This proximal displacement of the probe drive module 20 will, in turn, cause the transducer subassembly on the distal end of the probe element 16 to be longitudinally displaced proximally (i.e., pulled back away from) the distal-most end of the guide sheath 14.

The ultrasonic imaging scan is automatically terminated (e.g., by use of suitable limit switches and/or position transducers) when the probe drive unit reaches the its most proximal position as shown in FIG. 8C. In this connection, the present invention most preferably is provided with a limit switch (not shown) enclosed within a limit switch housing 29 (see FIGS. 4a and 5B) which is mechanically actuated when support flange 102 contacts support arm 112 (i.e., when the probe drive module 20 is in its most proximal position). The limit switch in housing 29 communicates electrically with the control console 46 via cabling 41. Virtually any suitable equivalent position-sensing devices could be employed in place of the limit switch. For example, the housing 29 could be sized and configured to accommodate an absolute position transducer so as to communicate absolute position to the control console 46. The information provided by such an absolute position transducer could be employed in conjunction with modified reconstruction algorithms for image reconstruction, even during manual operation of the probe drive module 20.

Upon the probe drive module 20 reaching its most proximal position, the pointer 24c associated with the positioning arm 24 registers with the marking "10" on the scale 60 of housing 22. Of course, the ultrasonic imaging scan need not necessarily be conducted over the entire range of 0–10 marked on the scale 60 and thus could be terminated at any time by the physician simply releasing the foot-switch 27 or by simply pivoting the probe drive module 20 into its manually-operable condition.

Those skilled in this art will recognize that a number of equivalent mechanical and/or electrical means could be employed. For example, locking slides, latches and quarter-turn screws could be used to allow engagement and disengagement of the probe drive module with the linear translation module. A flexible drive shaft connects the linear translation module to a rate-controlled motor which controls the automatic linear translation rate. The motor is most preferably located in a separate fixed base unit, but could be provided as in an integral part of the linear translation module, if desired.

Furthermore, various translation rates associated with the motor may be selected for various purposes. For example, slow rates give ample time for the physician to examine the real-time images in cases where time is not a limiting factor. The rate upper limit is governed by the probe rotation rate and the effective thickness of the imaging data slices generated by the probe, such that there is no (or an acceptable) gap between successive imaging data slices. This would prevent missing discernible features during vascular imaging with automatic translation. The effective thickness is governed by the ultrasonic beam characteristics of the probe. For some applications, the translation may be discontinuous (i.e., gated to an electrocardiogram) for use with modified algorithms or programmed to translate a fixed distance discontinuously.

Thus, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A imaging catheter comprising:

a motorized position translator coupled to a first end of a cable; and an imaging instrument coupled near the second end of the cable, the imaging instrument adapted for imaging within a patient's body;

wherein said position translator is adapted for both manual linear translation of the cable relative to the catheter and motor-driven linear translation of the cable relative to the catheter where during said motor-driven linear translation, said motorized position translator controls the rate of longitudinal translation of said imaging instrument.

2. The catheter of claim 1, wherein the position translator is electrically connected to a foot-activated switch to responsively effect said motor-driven linear translation of said cable when said switch is activated.

3. The catheter of claim 1, wherein the imaging instrument comprises an ultrasound transducer.

4. The catheter of claim 1, wherein the motorized position translator comprises a drive module, said drive module comprising a distally open-ended and longitudinally barrel-shaped housing and a positioning lever.

5. A method for imaging a patient's body cavity, comprising the steps of:

providing a catheter having a motorized position translator coupled to a cable, an imaging instrument being coupled to said cable, wherein said position translator is adapted for both manual linear translation of the cable relative to the catheter and motor-driven linear translation of the cable relative to the catheter;

positioning the catheter within a region of interest within the patient's body cavity; and translating the cable relative to the catheter during said motor-driven linear translation such that the rate of longitudinal translation of said imaging instrument is controlled by said motorized position translator.

6. The method of claim 5, wherein the step of translating the cable includes translating an imaging instrument.

7. The method of claim 6, wherein the step of translating the imaging instrument includes translating an ultrasound transducer.

8. The method of claim 7, further comprising the step of radially rotating the cable.

9. The method of claim 8, wherein the radial rotation is motor driven.

10. A method of performing an ultrasonic imaging scan comprising the steps of:

providing a catheter comprising a cable having an ultrasound transducer coupled to its distal portion;

providing a motorized position translator coupled to the cable, wherein said position translator is adapted for both manual linear translation of the cable relative to the catheter and motor-driven linear translation of the cable relative to the catheter;

positioning the ultrasound transducer in a region of interest within an anatomical structure of a patient;

radially rotating the cable thus rotating the ultrasound transducer; and activating the motorized position translator to effect linear translation of the ultrasound transducer wherein said motorized position translator controls the rate of longitudinal translation of said ultrasound transducer.

11. The method of claim 10, wherein the ultrasound transducer is in electrical communication with an ultrasound transceiver, said transceiver being in electrical communication with a monitor, and wherein the method further comprises the steps of:

receiving a signal transmitted by the ultrasound transducer, said signal being representative of the region of interest;

processing the signal by applying a display algorithm to said signal;

transmitting the processed signal to the monitor; and displaying an ultrasound image on the monitor, said image representative of the region of interest.

12. The method of claim 10, wherein the ultrasound transducer is in electrical communication with an ultrasound transceiver, said ultrasound transceiver being in electrical communication with a control console, wherein the method further comprises the step of using the control console to select operational parameters of the ultrasound transceiver.

13. The method of claim 10, wherein a control console is in electrical communication with the motor, and wherein the method further comprises the step of using the control console to select the linear translation speed of the motor.

* * * * *